US00PP26805P3

(12) United States Plant Patent
Klemm et al.

(10) Patent No.: US PP26,805 P3
(45) Date of Patent: Jun. 7, 2016

(54) *DIANTHUS* PLANT NAMED 'KLEDG13160'

(50) Latin Name: ***Dianthus* sp.**
Varietal Denomination: KLEDG13160

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 74 days.

(21) Appl. No.: 14/120,503

(22) Filed: May 27, 2014

(65) Prior Publication Data

US 2015/0351301 P1 Dec. 3, 2015

(51) Int. Cl.
*A01H 5/02* (2006.01)

(52) U.S. Cl.
USPC ..... Plt./272

(58) Field of Classification Search
USPC ..... Plt./272, 283, 278
See application file for complete search history.

(56) References Cited

PUBLICATIONS

Gabot Horticultural Portal News Search: Selecta novelties for IPM 2014, Dec. 30, 2013, retrieved on Oct. 22, 2015, retrived from the Internet at <http://www.gabot.de/index.php/DetailsIPM2014/566/0/?&no_cache=1&tx_ttnews%5Btt_news%5D=234482&cHash=59251ed3289a9792b488fb26db7b8850> 4 pp.*

Selecta Creating the future Selecta-Klemm Diantica, retrieved on Oct. 22, 2015, retrieved from the Internet at <http://www.selectaworld.com/en/selectaklemmproducts/products/dianthusdianticaR6.html 1> 6 pp.*

Taspo online Selecta Klemm: News and highlights for IPM Dec. 10, 2013, retrieved on Oct. 22, 2015, retrieved from the Internet at <http://taspo.de/messen/selectaklem-mneuheitenundhighlightszuripm/> 6 pp.*

* cited by examiner

*Primary Examiner* — June Hwu
(74) *Attorney, Agent, or Firm* — James M. Weatherly; Bethany R. Roahrig; Cochran Freund & Young, LLC

(57) ABSTRACT

A new *Dianthus* plant particularly distinguished by having single, red bicolored flowers, a compact growth habit, and strong branching, is disclosed.

1 Drawing Sheet

Genus and species: *Dianthus* sp.
Variety denomination: 'KLEDG13160'.

BACKGROUND OF THE NEW PLANT

The present invention comprises a new and distinct variety of *Dianthus*, botanically known as *Dianthus* sp. and hereinafter referred to by the variety name 'KLEDG13160'. 'KLEDG13160' is a selection that results from a cross pollination of the proprietary female *dianthus* line 'DSS 2008 0052' (unpatented) and the male *dianthus* line 'KLEDG13146' (U.S. Plant Pat. No. 25,877).

In June of 2009 the proprietary female *dianthus* line 'DSS 2008 0052' and the male *dianthus* line 'KLEDG13146' were cross pollinated in Stuttgart, Germany and seeds were obtained. The seeds were sown and plants were grown for evaluation. A plant line was selected in June 2010 in Stuttgart, Germany, and named 'KLEDG13160'. In June 2010, 'KLEDG13160' was first vegetatively propagated by vegetative stem cuttings. 'KLEDG13160' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Single, red bicolored flowers;
2. Compact growth habit; and
3. Strong branching.

CROSS REFERENCE TO RELATED APPLICATIONS

Plant Breeder's Rights for 'KLEDG13160' were applied for in in Europe with the Community Plant Variety Office on Jul. 1, 2013, application number 2013/1809. 'KLEDG13160' has not been made publicly available or sold more than one year prior to the filing date of this application.

DESCRIPTION OF THE PHOTOGRAPH

This new *Dianthus* plant is illustrated by the accompanying photograph which shows an overall view of the plant. The colors shown are as true as can be reasonably obtained by conventional photographic procedures. The plant is about 4 to 5 months-old grown indoors in Stuttgart, Germany in April 2011.

DESCRIPTION OF THE NEW VARIETY

The following detailed descriptions set forth the distinctive characteristics of 'KLEDG13160'. The data which define these characteristics were collected from asexual reproductions carried out in Stuttgart, Germany. Data was collected on four month-old plants grown in a greenhouse in Stuttgart, Germany in March 2014. Color references are to The R.H.S. Colour Chart of The Royal Horticultural Society of London (R.H.S.), 5th edition (2007).

Classification:
*Family*.—Caryophyllaceae.
*Species*.—*Dianthus* sp.
*Common name*.—Garden carnation.
*Variety*.—'KLEDG13160'.
Parentage:
*Female*.—The proprietary *dianthus* 'DSS 2008 0052'.
*Male*.—The *dianthus* 'KLEDG13146' (U.S. Plant Pat. No. 25,877).
Propagation:
*Type*.—Vegetative stem cuttings.
*Time to produce a rooted young plant*.—20 days.
*Root description*.—White, well-branched, fine.
*Rooting habit*.—Lanceolate.
Plant description:
*Plant form*.—Potted plant, upright, bushy, compact.
*Plant height*.—9.0 cm.
*Plant diameter or spread*.—15.0 cm.
Lateral branches:
*Length*.—5.0 cm.
*Diameter*.—2.0 cm.
*Internode length*.—0.5 cm to 2.0 cm.
*Internode number*.—3 to 5.
*Internode thickness*.—2.0 cm to 3.0 cm.
*Node length*.—0.3 cm.
*Node diameter*.—0.3 cm.
*Stem*.—Solid.
*Stem shape*.—Round.
*Texture*.—Smooth.
*Color*.—RHS N138B.
Foliage description:
*Arrangement*.—Opposite.
*Length*.—4.0 cm.
*Width*.—0.4 cm.
*Shape*.—Lanceolate.
*Apex*.—Acute.
*Base*.—Obtuse.
*Margin*.—Entire.
*Texture*.—Upper surface: Smooth.
*Venation pattern*.—Parallel.
*Color*.—Immature and mature leaves: Upper surface: RHS N138A. Lower surface: RHS N138B. Venation: RHS N138D.
Flower description:
*Flower type and habit*.—Single, round.
*Fragrance*.—Present.
*Natural flowering season*.—Spring to Fall.
*Flower longevity*.—Medium, 4 to 6 days.
*Position of flowers relative to foliage*.—Slightly above.
*Flower buds*.—Length: 1.2 cm. Diameter: 0.7 cm. Shape: Ovate. Color: Mixed, RHS 183C and RHS 137C. Extrusions of the style at bud stage: Absent.
*Corolla*.—Quantity of petals/arrangement: 5, radial. Corolla height: 1.0 cm. Petal length: 3.0 cm. Petal width: 1.8 cm. Petal shape: V-shaped. Petal apex: Obtuse. Petal base: Cuspidate. Petal margin: Slightly serrate; depth of margin very shallow. Petal texture: Upper and lower surfaces: Smooth. Petal color: Immature: Upper surface: RHS 59A to RHS 59C. Lower surface: RHS 64A. Mature: Upper surface: RHS 59A at the center and base with RHS 53C towards the edge. Lower surface: RHS 64C to RHS 64D.
*Calyx*.—Quantity of sepals/arrangement: 5, single. Calyx height: 1.3 cm. Calyx diameter, at the apex: 0.6 cm. Calyx shape: Cylindrical. Sepal apex shape: Cylindrical.
*Sepal texture*.—Upper and lower surfaces: Smooth. Sepal color: Upper surface: RHS 187B and RHS 137C. Lower surface: RHS 137B.
*Epicalyx*.—Position: Adpressed. Average length: 0.7 cm. Average width: 0.6 cm. Color: RHS 177A and RHS 136B. Apex shape: Obtuse.
Peduncles:
*Length*.—7.0 cm.
*Diameter*.—0.2 cm.
*Strength*.—Moderate to strong.
*Texture*.—Smooth.
*Color*.—RHS N138D.
Reproductive organs:
*Stamens*.—Quantity: Moderate to sparse. Filament length: 1.0 cm. Filament color: RHS 59A. Anther length: 0.2 cm. Anther diameter: 0.08 cm. Anther color: RHS 84D. Pollen amount: Moderate to sparse.
*Pistils*.—Quantity: 2. Pistil length: 1.6 cm. Style quantity per pistil: 2. Style shoulder: Absent. Style length: 0.1 cm. Style color: RHS 73D. Stigma shape: Filamentous. Stigma color: RHS 59A. Ovary size: 0.4 cm. Ovary shape: Ovate. Ovary color: Younger flowers are RHS 139D, mature flowers are RHS144C. Ovary texture: Smooth. Fruits/seeds: None observed to date.
Disease and insect/pest resistance: No special observations were made.

COMPARISON WITH PARENTAL LINES AND KNOWN VARIETY

'KLEDG13160' is a distinct variety of *dianthus*. 'KLEDG13160' is distinguished from its parents as described in Table 1:

TABLE 1

Comparison with Parental Lines

| Trait | Variety 'KLEDG13160' | Female parent 'DSS 2008 0052' | Male Parent 'KLEDG13146' |
|---|---|---|---|
| Flower type | Single | Double | Double |
| Growth | Compact | Medium to small | Medium |
| Branching | Strong | Less | Very strong |

'KLEDG13160' is most similar to the commercial *dianthus* plant named 'KLEDG11143' (U.S. Plant Pat. No. 23,150), commercially known as Everlast 'Burgundy Blush'. Differences between the two varieties are described in Table 2:

TABLE 2

Comparison with Similar Variety

| Trait | Variety 'KLEDG13160' | Commercial line 'KLEDG11143' |
|---|---|---|
| Flower type | Single | Double |
| Earliness | Medium | Medium to late |
| Branching | Strong | Medium |

We claim:

1. A new and distinct variety of *Dianthus* plant named 'KLEDG13160' as illustrated and described herein.

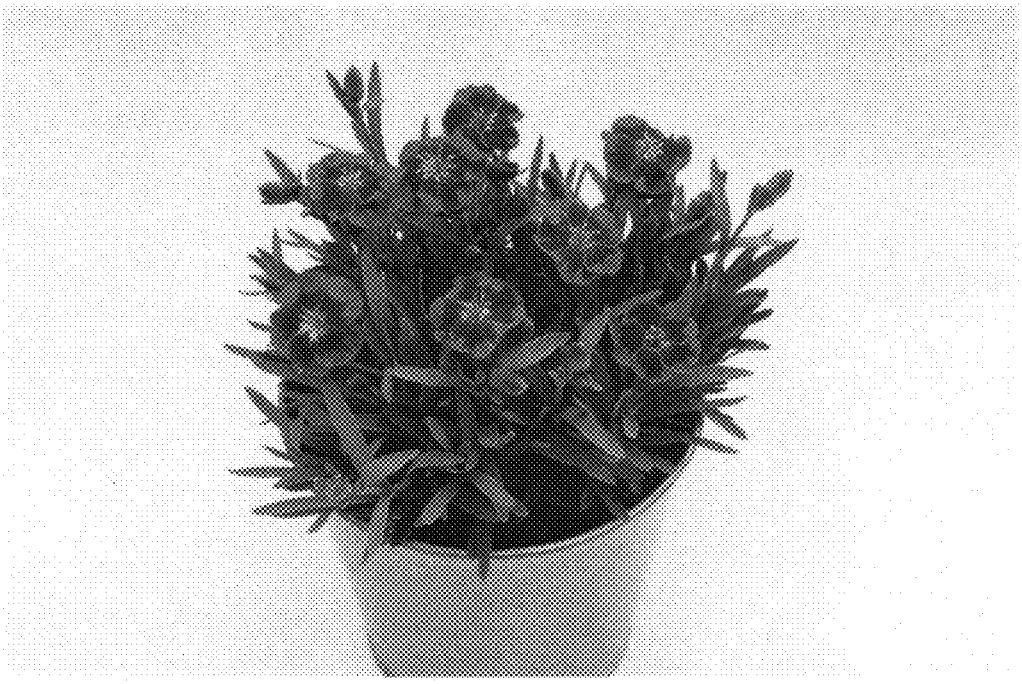

* * * * *